(12) United States Patent
Caraballo (10) Patent No.: US 9,993,315 B2
(45) Date of Patent: Jun. 12, 2018

(54) REMOVABLE LINGUAL-VESTIBULAR DENTAL ALIGNMENT DEVICE AND METHOD FOR THE PRODUCTION THEREOF

(71) Applicant: GENIOVA TECHNOLOGIES S.L., Madrid (ES)

(72) Inventor: Santiago Jimenez Caraballo, Madrid (ES)

(73) Assignee: GENIOVA TECHNOLOGIES S.L., Madrid (ES)

( * ) Notice: Subject to any disclaimer, the term of this patent is extended or adjusted under 35 U.S.C. 154(b) by 0 days. days.

(21) Appl. No.: 14/758,395

(22) PCT Filed: Jan. 2, 2013

(86) PCT No.: PCT/ES2013/000003
§ 371 (c)(1),
(2) Date: Jun. 29, 2015

(87) PCT Pub. No.: WO2014/106676
PCT Pub. Date: Jul. 10, 2014

(65) Prior Publication Data
US 2015/0335399 A1    Nov. 26, 2015

(51) Int. Cl.
*A61C 7/08* (2006.01)
*A61C 7/00* (2006.01)
(Continued)

(52) U.S. Cl.
CPC .................. *A61C 7/08* (2013.01); *A61C 7/00* (2013.01); *A61C 7/002* (2013.01); *A61C 7/12* (2013.01); *B33Y 10/00* (2014.12); *B33Y 80/00* (2014.12)

(58) Field of Classification Search
CPC .. A61C 7/08; A61C 7/00; A61C 7/125; A61C 7/146
See application file for complete search history.

(56) References Cited

U.S. PATENT DOCUMENTS

| 6,905,337 B1 | 6/2005 | Sachdeva |
| 8,356,993 B1 * | 1/2013 | Marston .................. A61C 7/08 433/24 |

(Continued)

FOREIGN PATENT DOCUMENTS

ES    2382967    6/2012

OTHER PUBLICATIONS

M. Garcia Bueno, International Search Report for PCT/ES2013/000003, dated Jul. 9, 2013, ISA/Oficina Espanola de Patentes y Marcas, Madrid, Spain.

*Primary Examiner* — Paula J Stice
(74) *Attorney, Agent, or Firm* — Trego, Hines & Ladenheim, PLLC; Brandon Trego; Jonathan Hines (57) ABSTRACT

The invention relates to a removable lingual-vestibular dental alignment device comprising an assembly of independent caps (12). The inner part of each cover (12) includes a fissure (14) for coupling to a fixing element (21, 24, and 27) adhered to the tooth (20) and outer elements (13) facilitating the passage of the dental arch (16) having a circular, square or rectangular section. The invention also relates to a method for the production of the caps (12) that includes scanning the mold of the denture and working on a virtual mold in order to include the corrective elements. The caps (12, 35) are produced after printing the result of the denture (9) with the different elements and subsequent stamping method or from the printing of a file corresponding to a virtual cap produced on the virtual denture (8) that includes the virtual cuboids (4) and virtual half-spheres (5).

7 Claims, 4 Drawing Sheets

(51) Int. Cl.
*A61C 7/12* (2006.01)
*B33Y 80/00* (2015.01)
*B33Y 10/00* (2015.01)

(56) References Cited

U.S. PATENT DOCUMENTS

2003/0190575 A1 10/2003 Hilliard
2010/0279245 A1 11/2010 Navarro

* cited by examiner

REMOVABLE LINGUAL-VESTIBULAR DENTAL ALIGNMENT DEVICE AND METHOD FOR THE PRODUCTION THEREOF

TECHNICAL FIELD

The present invention relates to a device for both the lingual and vestibular alignment of teeth. This invention is comprised in the sector of the art of orthodontics, particularly producing or maintaining the desired position of teeth, for example for straightening, leveling and aligning.

PRIOR ART

Spanish patent ES 2,382,967 entitled "Extractable dental alignment device" includes the known state of the art relating to devices based on braces which are attached to the denture through adhesives and with the aid of a high-strength or memory wire or arch. The operation of these devices is based on a wire with a desired dental arch shape so that once implanted in the braces, it applies a force on the braces that is transmitted to the teeth and thereby causes the movement of the teeth to the desired position. All these devices entail problems due to the discomforts they cause in the mouth of the patient, hygienic problems due to how difficult it is to clean them, particularly after meals, and problems relating to aesthetics.

Spanish patent 2,382,967 already indicates that "To limit the negative impact on a person's appearance, devices such as the known invisible aligner have been devised, which is based on an assembly of transparent plastic caps or dental prostheses having certain elasticity, which are placed covering the teeth and the dental prostheses gradually push the teeth towards a desired position . . . When the teeth have shifted due to the action of the dental prosthesis, and the dental prosthesis does not apply any more pressure on them, it is necessary to change the dental prosthesis for another one that continues to push the teeth to the desired position".

On the other hand, in relation to the methods for the production of a dental alignment device, the following documents are known in the state of the art:

Spanish patent 2,367,282, consisting of a method for producing a dental apparatus of the type previously described (page 3, lines 21 to 24 and FIG. 1C). This patent describes "a method for producing a dental apparatus (100), said method comprising: providing a set of digital data representing a modified arrangement of teeth for a patient; controlling a production machine (322) based on the sets of digital data to produce a positive model of the modified arrangement of teeth; and producing the dental apparatus (100) as a negative of the positive model." Furthermore, claim 2 provides that the step of control comprises: providing a volume of non-hardened polymer resin; scanning a laser to selectively harden the resin into a shape based on the set of digital data for producing the positive model.

Spanish patent 2,367,283, entitled "Method for producing a plurality of apparatus for the incremental regulation of the dental position," which relates to the production of dental apparatus of the type previously described, i.e., assembly of transparent caps or dental prostheses, (page 2, line 6 hereinafter and the claims).

Spanish patent 2,382,967 describes a first solution based on an assembly of caps to which there is manually adhered to cuboid-shaped tube or brace and which allows improving the position of the teeth by combining the technique of caps with dental arches and caps/braces, which confer greater force to the device for shifting teeth more quickly.

The described prior art documents do not solve the technical problem derived from choosing, and manually adhering on the actual device, the best location for positioning each brace and cuboid on the cap or caps. Currently, the doctor or specialized personnel places the braces on the teeth of the patient by hand, without having previously visualizing the alignment and the arch and the corresponding distribution of forces thereof. In other words, the choice and placement of braces is done by the expert or doctor by hand and based on their experience, without using a standardized method for doing so that allows assuring the correct choice and position of said elements.

DISCLOSURE OF THE INVENTION

The present invention shows a dental alignment device with improved caps as well as a method for the production thereof which solves the preceding problems. The method for production is based on using a virtualization system to design the caps and choose the best arrangement of the elements forming it (braces and cuboids), as well as automation in the method for the production of the caps and, where appropriate, the cuboid projections through which the dental arch passes. The choice of the position of the caps or braces in the caps is made by a specialist with the aid of specific machinery that includes virtualization programs. Producing the devices based on caps which have the cuboids through which the arch passes integrated in the lingual or vestibular part is done automatically with the aid of specific devices. This method seeks to eliminate human errors of ocular perception when choosing the location of braces, as well as errors derived from manually performing this technique.

The teeth corrective device is made up of an assembly of caps. Each cap adapts to the tooth or teeth anatomically and aesthetically due to its transparency. Each cap incorporates one or several elements placed in the vestibular area or lingual area, with the force messages of torque, inclination and angulation to generate three-dimensional control in the dental movement based on incorporating a nickel-titanium arch, equivalent to those used in fixed apparatus but applied to caps, which allows working in a removable manner. These elements can be braces or cuboids adhered to the caps at a specific point, as well as in cuboids built in the actual body of the cap during the method for the production thereof.

To that end, the device object of the patent is based on combining the use of the high-strength arch and brace technique with the use of teeth caps. Therefore, there are two embodiments of the invention as well as the method for the production thereof.

First Embodiment of the Device

The device is made up of an assembly of independent caps which are fitted on a tooth or several teeth and to which the expert adheres the braces and cuboids having certain dimensions in a previously predetermined position. When using cuboids, it will have certain dimensions according to the position in which it is located. This device can include braces and cuboids in the vestibular part or lingual part. In any case, a distinction is made between:

Individual caps which are individually fitted on teeth to correct their position and to which a brace or cuboid is adhered.

Caps used as a fixing element and they are used on a single tooth or on several teeth, which is common for molars. In the latter case, only one brace or cuboid through which the arch passes is included and it is used as a point of support on the denture and so that the arch applies force on the teeth to be shifted.

The braces or cuboids are adhered to the individual caps in positions previously determined by means of a virtualization process on the denture of the patient and the cap or caps which are fixed to the teeth of the patient. As a result of the process for production, the caps include a linear protrusion to indicate to the doctor the position in which the braces or cuboids must be adhered. The high-strength arch, in which the ideal dental arch of the patient has previously been memorized, applies constant forces on the braces and cuboids which are transmitted to the corresponding caps through their fixing elements previously defined through the linear protrusion, and through the latter to the teeth, causing the corresponding correction.

The memory of the arch is determined by the material used to produce it, steel and nickel-titanium being used. With the force applied on the arch and the direction in which it is applied with the aid of the braces and cuboids on the caps, position of the teeth is improved, particularly in adults, and when the teeth must be shifted a significant distance, i.e., more than 0.5 millimeters. For finer adjustments, more specific techniques, such as invisible aligners, can be used. This technique allows an adult to rapidly take off the device themselves.

A notch is made in the inner part of the caps having a negative shape for housing fixing elements, such that these notches will be used for positioning and fixing each cap to the tooth and preventing the involuntary vertical shifting of the caps once they are located on the teeth.

The fixing elements have a specific geometry and are adhered directly to the teeth in a specific position. The geometry of these fixing elements is designed to facilitate the positioning of the cap on the tooth as well as to safely couple and uncouple it without causing injuries in the mouth. There are two types of fixing elements for the caps object of this invention.

a) "Turned"-type in which the closing is done based on bevels or projections. This closing consists of a rectangular figure from which there emerge bevels or projections tilted and oriented with a certain tangency to a half-sphere located in the central part thereof and taking in each of these projections in a specific direction forming a rotation. The elevation of the projections in their path towards the half-sphere, together with their orientation will apply the mechanism for closing the fixing element with the caps. A fixing element turned in the clockwise direction and a fixing element turned in the counterclockwise direction is produced according to the direction of the bevels.

b) Vertical-type in which the closing is based on the combination of four basic elements:
  a. Truncated sphere in the upper part which is attached to the cervical area of the tooth so that the cap does not remain coupled. The sphere projects from the top part of this closing to protect the tongue from possible lesions occurring due to contact thereof with this closing,
  b. Outer vertical rectangular cuboid
  c. Horizontal rectangular cuboid creating the flap for coupling the cap to the tooth and not allowing the shifting thereof, vertically coupling with the cap.
  With the combination of the two cuboids, the cap can only be taken off the tooth through a specific vertical movement.
  d. Cylinder compressed in the form of a pellet which is adhered to the tooth. The diameter of this cylinder is greater than the length of the vertical cuboid in order to protect the tongue from possible lesions occurring due to contact with the tissues of the mouth.

The method for the production of this device is performed with the aid of electronic devices, computers and specific programs. The expert adheres the braces and cuboids he/she previously defines, with the aid of these electronic devices, the position in which said elements must be adhered by means of virtualization of the denture of the patient to which the corresponding virtual caps are added. Once the position is chosen, each of the braces and cuboids is manually adhered. Therefore, the method for production eliminates a large part of the work done by hand.

This solution solves the following problems:
a) In relation to invisible aligner patents, this device allows correcting the position of the teeth in less time due to the force applied by the arch. Furthermore, in this case only one device is used, which prevents having to change the invisible aligner each month.
b) In relation to the current technique for correcting the position of teeth using braces, like in Spanish patent 2,382,967, the problems of directly adhering braces to teeth and manipulating them to introduce the arch into the braces once they are adhered to the teeth are prevented. Furthermore, other specific and more discreet cuboids can be used to achieve the same effect, because it is not possible to use devices such as cuboid-shaped tubes adhered to the teeth.
c) In relation to Spanish patent 2,382,967, this new invention is based on defining prior to the inclusion of braces or tubes the plane that is common to all of them. For this reason, all the caps are marked with a linear projection indicating the plane of alignment for the braces and cuboids. Secure alignment of the teeth is thereby obtained, preventing human errors of ocular perception when the location in which cuboids or braces must be adhered is to be chosen. Furthermore, the inclusion of the fixing elements secures the caps on the teeth, improving the corrective effect of the device.

The caps, like dental prostheses used in orthodontics, are placed in the mouth with the aid of the patient's own hands, and they can be readily taken off without any special technique. The caps are made of a very strong and elastic material, such as hard plastics or methacrylate, such that when fixed on each tooth or a set of teeth, they adapt to the geometry of the tooth and apply enough pressure to be immobilized on them. The positioning of the caps and the force applied by the arch in the necessary direction is established when it is placed in the mouth. This device allows being worn in the mouth or stored in a case.

Second Embodiment of the Device

Like in the preceding case, the corrective device is made up of an assembly of independent caps which can be fitted on a single tooth or on a set of teeth, individual caps being fitted on teeth to correct their position and caps used as a fixing element being distinguished from one another. In this case, the device is made up of an assembly of caps made from a plastic material which includes in the actual body of the caps cuboids having certain dimensions located in the position chosen by the expert during the method for the production thereof. Like in the preceding case, this device can include cuboids in the vestibular part or lingual part.

The method for production eliminates a large part of the work done by hand because the expert chooses the position of said tubes and the dimensions thereof by means of virtualization of the denture of the patient to which the corresponding virtual caps are added. Then, based on the choice of the expert, the automated production of the caps takes place, including in the actual body thereof tubes through which the arch which applies force on the caps to correct the position of the teeth passes.

In other words, the cuboid projections are part of the caps. Therefore, in this case, braces which are adhered to individual caps are not used. Both the positioning of the cuboids and their dimensions are previously determined by the expert by means of a virtualization process on the denture of the patient and the caps. So for the arch to more effectively apply force on the tooth, the expert determines the height of the cuboids and the location of each of them with the aid of virtualization programs to achieve greater precision. The resulting caps therefore include the cuboid projection at the height where the expert considers that the arch must pass. A perforation through which said arch passes is made in said cuboid projection.

In addition to the problems raised above, this solution solves the following problems:

- A cuboid projection having specific dimensions is made for each cap for producing the best result derived from the force applied by the arch on the cap.
- All the cuboid-shaped projections are aligned in one and the same plane, preventing the problems of manipulation and errors of ocular assessment in the positioning of the cuboids due to perspectives as a result of the different positions of teeth.
- This method assures exact alignment of the arch, because the arrangement of the cuboids is performed previously through the virtualization method.
- Since the caps and their cuboids are made in a single body, the visual impact of the device is reduced, being better accepted by users. Furthermore, the step of having to adhere the braces to the teeth or caps is eliminated.

Method for production. The alignment device is produced by means of the following steps:

1) Once the denture model of the patient has been obtained through a standard method using standard bite wax, the model taken from the patient is scanned three-dimensionally. A set of digital data representing the denture of the patient is produced through a laser scanning method of said mold. This digital data represents the geometric characteristics of the denture of the patient, which will be used to virtually represent said denture and to be able act on it. The scanning method is not described in further detail because it is known in the state of the art, as described in the Written Opinion for Spanish patent 2,372,190, page 4/6.

2) The set of digital data representing the scanned model is sent to a computer program which virtualizes the denture model of the patient. On this virtualized model, the expert can add and modify the different virtual elements that are added to virtually create in a customized manner the dental alignment device. To that end the following steps are performed:

a. Creating square prisms or cuboids having virtual sections. Based on a library of virtual cuboids, cuboids having a pyramidal base are chosen and modified in a customized manner for each tooth of the patient. These virtual cuboids will be used to later define the cuboid projections of the caps through the inner portion of which the arch passes. The key to the success of these devices is in the specific design for each tooth according to the movement sought as well as the placement thereof.

b. Choosing the virtual horizontal insertion plane in which the cuboids are placed in an aligned manner. A horizontal plane which cuts the teeth on a virtual cutting line is established with the aid of a specific program. The choice of the plane and determination of the cutting line establishes the height at which the expert controls in a calibrated manner the positioning of the virtual cuboids which are incorporated on each tooth, creating a horizontal discontinuity according to squeezing, which is what gives rise to the securing of the apparatus in the mouth of the patient.

c. Placing the virtual cuboids. Once the horizontal insertion plane is selected, the virtual cuboids are placed in said plane on each of the virtual teeth. As described in paragraph "a", each cuboid is customized according to the part in which the cap will later be inserted and on which movement must occur. In this case, the idea is for the arch to apply a force on the cuboid (at this point a virtual prism or cuboid having a section projecting from the tooth) generating a second message of movement consisting of inserting into the tooth the section having a non-uniform shape according to the poor position of the tooth. In other words, the cuboid will be longer or shorter, have a greater or lesser depth or height, being inserted more or less with respect to each side, to be able to generate the desired movement in the tooth. Disparity is therefore created in the positioning and dimensions of the virtual cuboids, which will be more or less according to the movement to be made. Through virtualization, the different cuboids can be placed and the corresponding tests can be conducted to choose the best combination and thereby increase the effect generating the force applied by the arch on the tooth when acting through the cuboid and cap.

The cuboids can be positioned in the lingual part, vestibular part or a combination of both, because when they are combined the generated force is greater. This positioning is determined by the movement to be made and the "poor positions" of the teeth.

The cuboids are positioned following a placement technique based on balance, torques and angulations, because the objective that is sought is for the forces applied by the arch to be transmitted to the caps and teeth the same way the braces do.

d. Vertically controlling the caps. To improve the fixing element for fixing the caps on the teeth and to prevent shifting of the caps due to the forces to which they can be subjected, some cavities are made on the inner portion of some caps to allow the fixing elements adhered directly to the tooth to be inserted in them. The fixing elements are positioned through virtualization of the teeth. In this step, the expert or doctor chooses the type of fixing element to be used on each tooth based on virtual models stored in a computer and indicates the position of the virtual teeth where future fixing elements must be adhered. To that end, virtual half-spheres, the diameter of which can be modified to adapt it to the cap and specific tooth, can be used or the specific fixing element can be used.

e. As a result a computer file, for example an STL-type file, which includes all the geometric characteristics of the virtual denture, including a relative line with respect to the horizontal virtual plane, an assembly of cuboids having different dimensions and virtual half-spheres for the future control of the caps, is produced.

3) Printing. Three-dimensional (3D) printing is performed from the computer file including the data relating to the virtual denture, its cuboids, horizontal plane and caps. A model of the teeth of the patient including the cuboids and fixing elements is thereby produced. This model of the teeth is the equivalent to the negative of the caps and caps to be produced.

4) Stamping the cap. A transparent thermo-molding plate of 0.5 to 1.5 millimeters is stamped on this mold. To that end, a conventional stamping method based on using a pressing machine that adapts the methacrylate, resin acetate, ceramic, zirconium plates, etc., to the model, giving rise to the cap, is used. The thickness is determined by the dental movement to be made as well as the force to which the caps are subjected, and therefore the force to be transmitted. As a result of stamping, a cap with the positive form of the model, the shape of the teeth and the cuboid with the section of opening of each cap is produced.

5) Opening sections and producing the alignment device. At this point, the cuboids are opened on both sides, creating an open section of the preform attached to the tooth. The opening can be made with drills and a micromotor or by inserting a hot rectangular arch. An arch having a round or circular section is then slid through each opening made in the cuboids of each cap, interconnecting all the caps and securing them with an elastic fastener.

A variant of the preceding method consists of adding a step of the virtual production of caps after step 2.d. In this case, after virtually designing the caps with their components based on the work done on the virtual denture, volume is provided and it virtually reproduces the cap with a thickness comprised between 0.5 and 1.5 millimeters. A file (step 2.e) with the digital data of the cap with the recess for fixing element and cuboid projection is thereby produced. This file allows being able to produce the cap according to requirement of the patient (acrylic, ceramic or zirconium), allowing it to be done later through a 3D printer using the desired material and by combining the desired aesthetic characteristics. This variant eliminates the step of printing the denture as well as the step of stamping the caps on the printed denture.

The device that is produced is a device or apparatus generating dental movements based on individual caps of each tooth in which each cap includes a projection having a square or rectangle section corresponding to a cuboid. Since the caps are interconnected with a flexible arch that passes through the opening of the cuboids resulting from the sections generated during virtualization, the same force messages generated by conventional braces are simulated, producing the same movements in the teeth but without using the braces adhered to the teeth.

This device is removable and more aesthetic than the direct use of braces because it is based on the use of transparent caps which, since they take in the entire clinical crown, allows transmitting the forces of the flexible arches without having to adhere the braces. The device is therefore more hygienic, comfortable and aesthetic.

This method for production improves the solution described in patent document 2,382,967 for removable braces because since it uses the method based on virtualization of the denture of the patient, it prevents using a brace as a connecting element between the arch and the cap. This method virtually generates a modified model of the patient with all the virtual components incorporated so that once it is prototyped a cap that reproduces these components in a transparent manner can be generated, thereby preventing the use of braces.

The advantage of this method for production consists of producing computer files containing the information about the denture and the negative form for the production of the caps with their protrusions. Information for producing an entire device in case of loss, or only one of the caps in case of partial breaking of the devices, can be readily retrieved with these files.

Another variant in the method for the production of the device consists of limiting the production of the caps including a line indicating the virtual horizontal plane corresponding to the location of the cuboids. In this case, the method is the same excluding the cuboid selection process and the inclusion thereof in the step of virtualization of the denture. In other words, the horizontal plane will be defined and, where appropriate, the places where the braces must be adhered will be marked in this step. In the step of printing, the horizontal plane will be shown by a line in the denture acting as a negative form, like the points where the braces must be adhered. When performing the method for stamping the caps, the corresponding line and place where the braces must be adhered will be shown with discreet mark but one that can be seen by the expert. A variant of this process for production is the production of virtual caps. From this variant, a prototype of the caps can be virtually designed from the virtual model. The virtual caps will be useful as a model for later printing the caps and they are stored in a digital data file. From here, the doctor, with the aid of the mark of the cutting line containing the caps, then adheres the braces in the desired position. This method is less expensive but done by hand.

DESCRIPTION OF THE DRAWINGS

The following drawings are enclosed for better understanding.

DETAILED DISCLOSURE OF THE INVENTION

Figure 1:
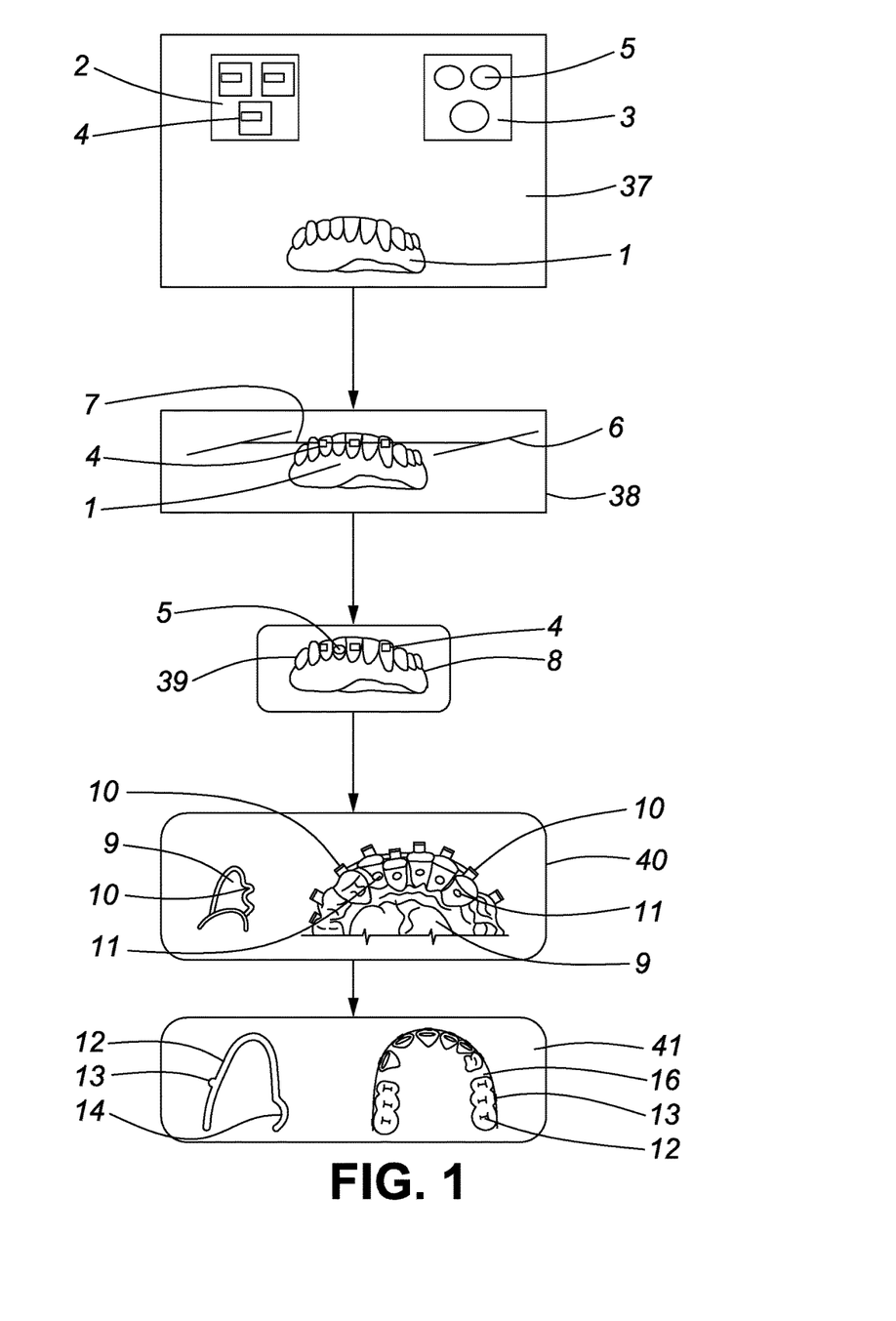
FIG. 1 depicts a flow diagram of the method for the production of a dental alignment device.

FIG. 1 shows the virtual denture (1) produced from the scanning performed on the denture model of the patient which consists of a set of digital data and is shown in a graphic computer program. In the first step (37) it shows having access to a virtual library (2) of virtual cuboids (4) having different dimensions and another library (3) with virtual fixing elements (5) having different dimensions and geometries. When choosing a cuboid (4) and virtual fixing element (5), the dimensions thereof may be modified to adapt it to the virtual tooth of the virtual denture (1). Based on the image of the virtual denture (1) the doctor then chooses and represents the horizontal virtual plane (6), step (38). The placement of the plane produces a cutting line (7) with the virtual denture. This cutting line will indicate the height at which the virtual cuboids (4) chosen in the library (2) must be placed, and where appropriate, the geometry thereof is modified. The positioning of the plane and generation of the cutting line (7) is also used to show the height at which the braces (32) must be placed. Once the virtual cuboids (4) are placed, with the aid of the program the doctor manipulates the positioning and the final dimensions of the cuboids (4) until achieving the result that is sought. In this case, the idea is for the arch (16) to apply a force on the virtual cuboid so that it generates certain force and message of movement in the tooth (20). Through virtualization, the different virtual cuboids (4) can be placed and the corresponding tests can be conducted to choose the best combination and thereby improve the effect the actual arch (16) will later apply on the tooth (20) when it acts through the cuboid projections (13) of the cap (12). This step (37) shows the vestibular placement of the virtual cuboids (4), although lingual placement is also possible.

Figure 2:
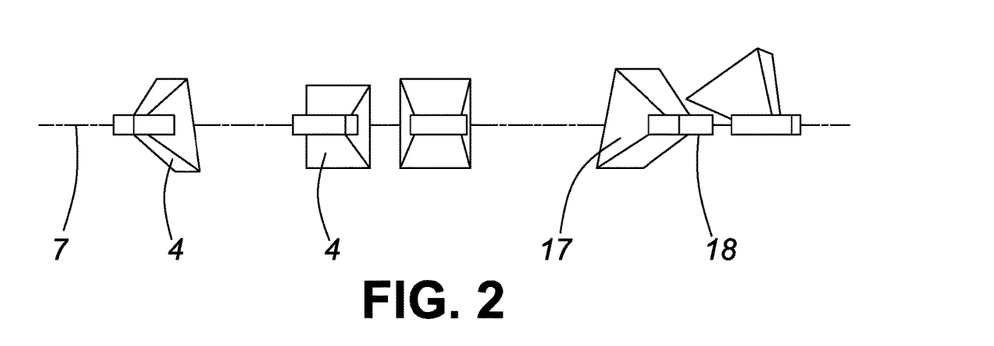
FIG. 2 shows the positioning of virtual cuboids in relation to the balance line based on the virtual cutting line.

The doctor will then virtually balance the forces applied by the arch (16) on each of the actual teeth (20) with the aid of a virtual view of the positioning of the virtual cuboids (4) in relation to the virtual cutting line (7) corresponding to the balance line as shown in FIG. 2. This method can also be applied to braces, not shown in the drawings. The virtual cuboids (4) are positioned following a placement technique based on balance, torques and angulations, in order to get the forces that will be applied by the arch to be transmitted to the caps (16) and teeth (20) the same way the braces do.

To vertically fix the actual caps (12), half-spherical virtual projections (5) are inserted in the positions of the teeth where the fixing elements (21, 24, and 27) will later be manually adhered on the actual denture. These fixing elements (21, 24, and 27) are defined by choosing the corresponding fixing elements from a virtual library and then modifying their dimensions and geometry to adapt them to each tooth and cap. Neither these libraries nor the definition of the fixing elements have been depicted in the drawings.

Figure 13:
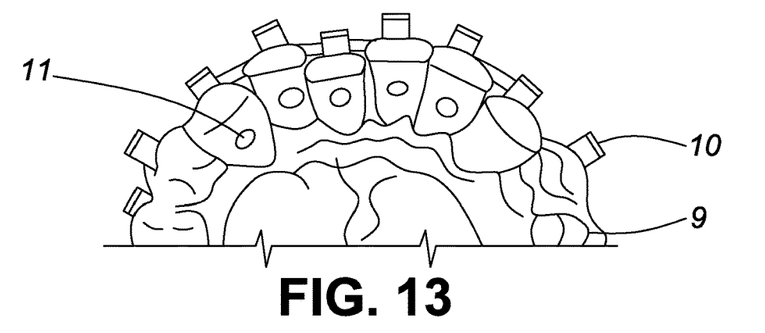
FIG. 13 shows a virtual denture in which the doctor has placed virtual cuboids following the positioning line and spheres for making a depression in the caps.

FIG. 13 shows the final virtual result where the virtual denture (8) includes the virtual cuboids (4) following the cutting line (7) and spheres (5) for making a depression in the caps.

As a result of the virtual method, a computer file is produced, step (39), with the geometric characteristics of the virtual denture (8), including the cutting line (7), an assembly of virtual cuboids (4) having different dimensions which are linked to the denture (8) and virtual half-spheres (5) for future control of the caps (12). This file (39) is printed with a 3D printer, step of printing (40), producing a model of the teeth or printed denture (9) of the patient including cuboid-shaped projections (10) and half-spherical projections (11). A method of stamping is performed on this printed denture (9), step of stamping (41), for producing the final caps (12) with the shape of the teeth and including cuboid projections (13) and notches (14) for housing the closing of the fixing elements (21, 24, and 27). The corresponding gap is made on the cuboid projections (13) with drills and a micromotor or by inserting a hot rectangular arch. A dental arch (16) having a rounded or circular section is then slid through each opening made in the cuboids of each cap, interconnecting all the caps and securing them with an elastic fastener.

Figure 3:
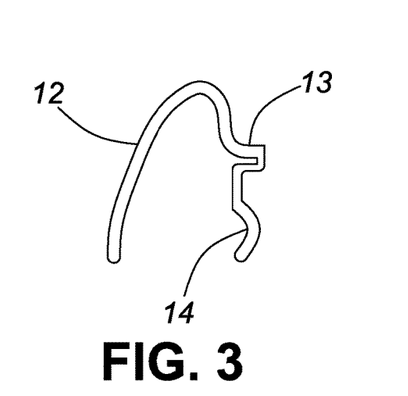
FIG. 3 shows a profile view of a cap resulting from the method for the production thereof.

Each cap (12), FIG. 3, has the shape of the tooth (20) produced after the method for the production thereof. In the vestibular part or lingual part, it includes a cuboid-shaped projection (13) as well as a fissure (14) which allows fitting the cap (12) on a fixing element (21, 24, and 27) adhered to the tooth (20) to which the cap (12) is coupled. The position of each fissure (14) is defined in the virtualization method as shown in FIG. 1.

Figure 4:
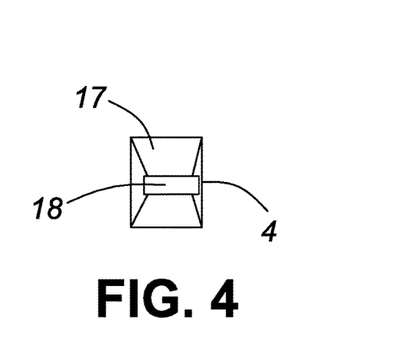
FIGS. 4 and 5 are two views of virtual cuboids used in the method for the production of the caps.
Figure 5:
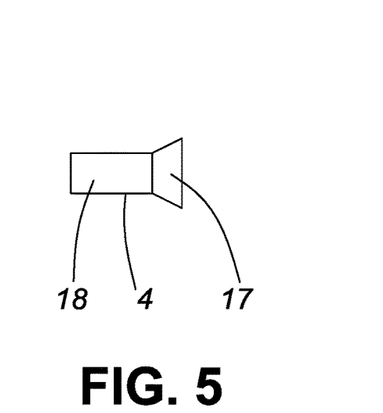

The virtual cuboids (4), FIGS. 4 and 5, have a wider prismatic base (17) on which there rests the rectangular prism (18) the dimensions of which are determined by the doctor according to the force, including direction thereof, that the arch (16) must apply on each tooth (20). When printing the caps (12) these cuboids produce the corresponding projection (13) in the cap (12) forming a single body, as shown in FIG. 3.

Figure 6:
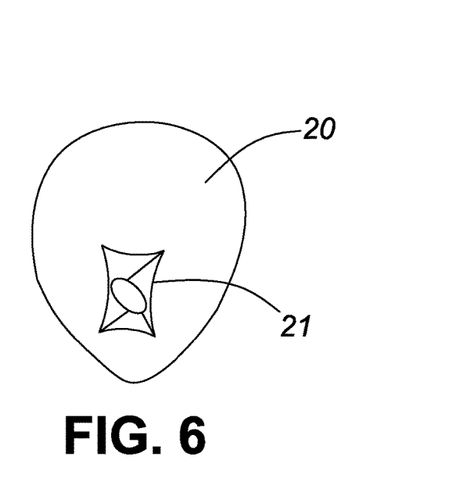
FIG. 6 shows a view of a turned-type fixing element for fixing on a tooth.
Figure 7:
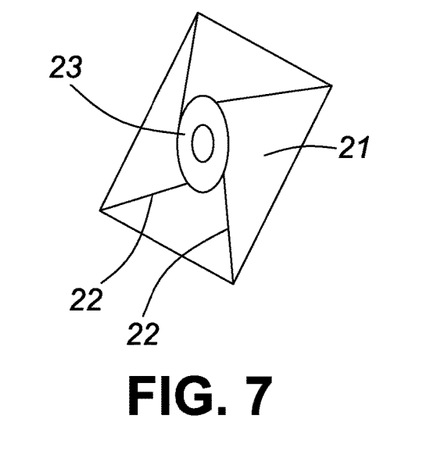
FIGS. 7 and 8 show perspective views of a turned-type fixing element with clockwise rotation and counterclockwise rotation.
Figure 8:
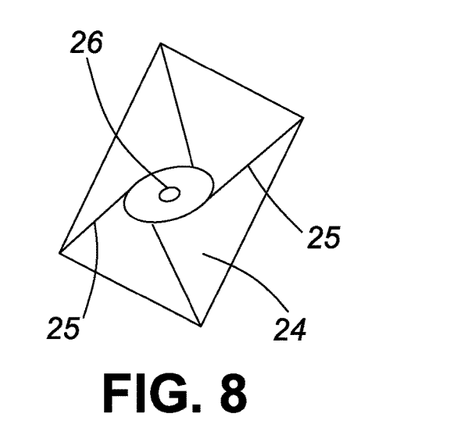

The doctor manually adheres the fixing elements (21, 24, and 27) to the teeth (20) in the position previously determined for making the notch in the caps (12). Therefore, FIG. 6 shows a turned-type fixing element (21) adhered to the lingual part of a tooth (20). As shown in FIGS. 7 and 8, such "turned"-type fixing element (21, 24) consists of a rectangular figure from which there emerge bevels (22, 25) or projections tilted and oriented with a certain tangency to a half-sphere having an elliptical section (23, 26) located in the central part thereof and taking in each of these projections (22, 25) in a specific direction forming a rotation. The elevation of the projections (22, 25) in their path towards the half-sphere (23, 26) together with their orientation will apply the mechanism for closing each fixing element (21, 24) with the caps (12) to make the corresponding fixing element. FIG. 7 shows the case of a fixing element (21) with projections with a clockwise rotation, whereas FIG. 8 shows a fixing element (24) with counterclockwise projections (25).

Figure 9:
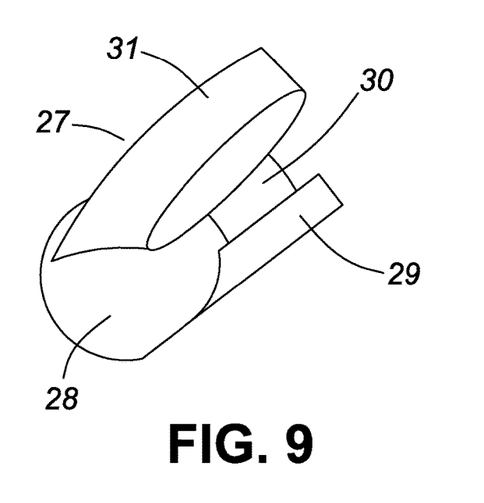
FIGS. 9, 10 and 11 show plan and profile view of the vertical-type fixing element.
Figure 10:
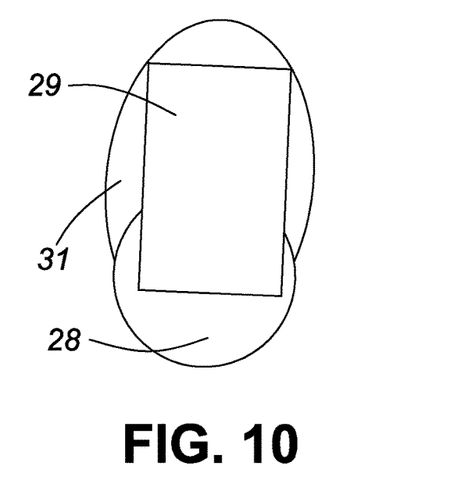
Figure 11:
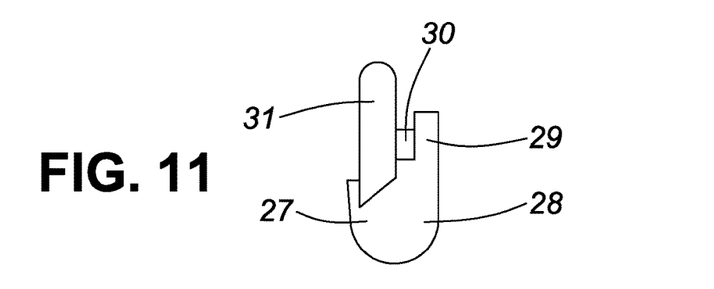

The vertical-type closing (27), FIGS. 9 to 11, consists of:
- A truncated sphere (28) in the upper part which is attached to the cervical area of the tooth so that the cap (12) does not remain coupled. The sphere projects from the top part of this closing to protect the tongue from possible lesions occurring due to the contact thereof with this closing.
- An outer vertical rectangular cuboid (29) and a horizontal rectangular cuboid (30) creating the coupling flap for coupling the cap to the tooth.
- A cylinder (31) compressed in the form of a pellet which is adhered to the tooth (20). The diameter of this cylinder (31) is greater than the length of the vertical cuboid (29) to protect the tissues of the mouth.

The closings are produced by a method of stamping based on the computer files representing the closings and they have been defined in steps (33 and 34).

Figure 12:
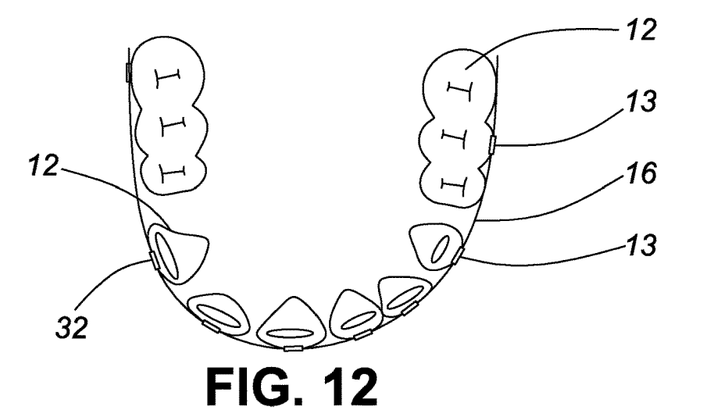
FIG. 12 shows the resulting alignment device.

FIG. 12 shows the final result of this method which consists of an assembly of caps (12) forming a corrective device for correcting the position of the teeth with the aid of an arch (16). Independent caps (12) can be fitted on a single tooth (20) or on a set of teeth. Each of the caps (12) includes a brace (32) or a perforated cuboid-shaped projection (13) which is traversed by an arch (16) which applies force on the cuboid projection (13) which is transmitted to the cap (12) through the cuboid. As a result, the cuboid will have certain shape and dimensions according to the desired direction of the force to be applied on the tooth.

Figure 14:
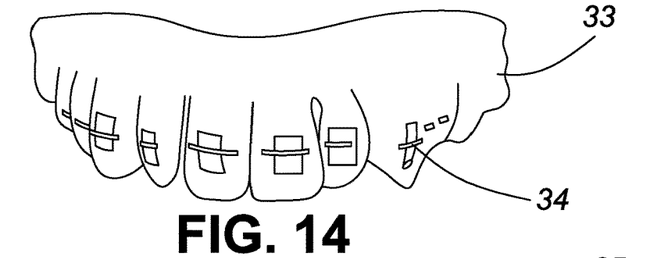
FIG. 14 shows a printed denture including a straight projection corresponding to a cutting line.
Figure 15:
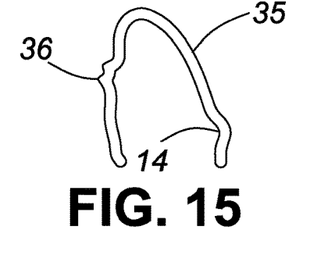
FIGS. 15 and 16 show two caps with the cutting line in opposite positions.
Figure 16:
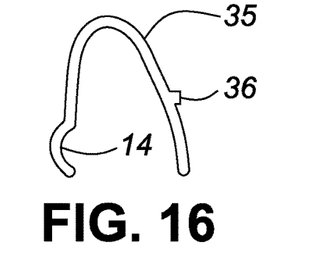

FIG. 14 shows the variant corresponding to a printed denture (33) including a straight projection (34) corresponding to the cutting line (7). This denture (33) is distinguished from the denture (9) in that it does not include cuboid projections (10). The caps (34), FIGS. 15 and 16, that are produced by the stamping of this denture (33) will only include a protrusion corresponding to a projection (35) which indicates to the expert the height at which the braces or cuboids can be manually adhered as well as the notch (14) for housing the fixing elements (21, 24, and 27).

INDUSTRIAL APPLICATION

This invention can be applied in the industry relating to health sciences, particularly the sector of orthodontics.

The invention claimed is:

1. A removable dental alignment device comprising an assembly of independent caps (12, 35) covering at least one tooth (20), a geometry of each cap (12, 35) being substantially identical to a geometry of the at least one tooth (20) it covers, characterized in that an inner part comprises a fissure (14) for coupling to a fixing element (21, 24, 27) adhered to the tooth (20) and at least one outer element facilitating a passage of a dental arch (16) having a section to be chosen from circular, square and rectangular, wherein each cap (12) comprises a cuboid-shaped projection (13) comprising a prismatic base (17) that is wider than a perforated rectangular prism (18) resting on the prismatic base (17), such that the dental arch (16) passes through the perforated rectangular prism (18).

2. The removable dental alignment device according to claim 1, characterized in that caps (35) have marked thereon a straight protrusion (36) on which there are adhered braces (32) or cuboids (13) with a prismatic base (17) and perforated rectangular prism (18) through the inner portion of which the dental arch (16) passes.

3. The removable dental alignment device according to claim 1, characterized in that fixing element (27) is of a vertical-type and consists of:
   a projecting truncated sphere (28),
   a coupling flap formed by an outer vertical rectangular cuboid (29) and a horizontal rectangular cuboid (30),
   a protective cylinder (31) compressed in the form of a pellet a diameter of which is greater than a length of the vertical cuboid (29).

4. The removable dental alignment device according to claim 1, characterized in that the fixing element (21, 24) is of a turned-type and is adhered to the tooth and consists of a rectangular figure from vertices of which there emerge projections (22, 25) tilted and oriented with a certain tangency to a half-sphere having an elliptical section (23, 26) located in a central part thereof and taking in each of these projections (22, 25), and in that the projections (22) form a clockwise rotation.

5. The removable dental alignment device according to claim 4, characterized in that the projections (25) form a counterclockwise rotation.

6. The removable dental alignment device according to claim 1, characterized in that the cuboid-shaped projections (13) are located in a vestibular part of the caps (12).

7. The removable dental alignment device according to claim 1, characterized in that the cuboid-shaped projections (13) are located in a lingual part of the caps (12).

* * * * *